US006231597B1

(12) United States Patent
Deem et al.

(10) Patent No.: US 6,231,597 B1
(45) Date of Patent: May 15, 2001

(54) APPARATUS AND METHODS FOR SELECTIVELY STENTING A PORTION OF A VESSEL WALL

(76) Inventors: Mark E. Deem, 240-C Liberty St., San Francisco, CA (US) 94114; Timothy W. Malisch, 6217 N. Meredith Ave., Chicago, IL (US) 60646

( * ) Notice: Subject to any disclaimer, the term of this patent is extended or adjusted under 35 U.S.C. 154(b) by 0 days.

(21) Appl. No.: 09/250,710

(22) Filed: Feb. 16, 1999

(51) Int. Cl.⁷ ............................................... A61M 25/092
(52) U.S. Cl. ...................... 623/1.12; 623/1.11; 606/108
(58) Field of Search .................... 606/198, 108, 606/200, 151, 153, 154, 190, 191, 195; 623/1.12, 1.11, 1.23

(56) References Cited

U.S. PATENT DOCUMENTS

| | | | |
|---|---|---|---|
| 5,041,126 | * 8/1991 | Gianturco | 606/195 |
| 5,104,404 | * 4/1992 | Wolff | 623/1 |
| 5,122,136 | 6/1992 | Guglielmi et al. | 606/32 |
| 5,135,536 | 8/1992 | Hillstead | 606/195 |
| 5,192,307 | 3/1993 | Wall | 623/1 |
| 5,259,366 | * 11/1993 | Reydel et al. | 128/4 |
| 5,263,964 | * 11/1993 | Purdy | 606/200 |
| 5,314,444 | 5/1994 | Gianturco | 606/195 |
| 5,342,387 | 8/1994 | Summers | 606/198 |
| 5,354,309 | 10/1994 | Schnepp-Pesch et al. | 606/198 |
| 5,443,500 | 8/1995 | Sigwart | 623/1 |
| 5,540,712 | * 7/1996 | Kleshinski et al. | 606/198 |
| 5,607,445 | * 3/1997 | Summers | 623/1 |
| 5,643,314 | 7/1997 | Carpenter et al. | 606/198 |
| 5,702,419 | * 12/1997 | Berry et al. | 606/198 |
| 5,772,668 | * 6/1998 | Summers et al. | 606/191 |
| 5,776,142 | * 7/1998 | Gunderson | 606/108 |
| 5,843,172 | * 12/1998 | Yan | 606/198 |
| 5,989,230 | * 11/1999 | Frassica | 604/264 |

FOREIGN PATENT DOCUMENTS

| | | |
|---|---|---|
| 98/39055 | 9/1998 | (WO) . |
| 98/49983 | 11/1998 | (WO) . |
| 98/50102 | 11/1998 | (WO) . |

OTHER PUBLICATIONS

Ajay K. Wakhloo, et al., "Self–Expanding and Balloon–Expandable Stents in the Treatment of Carotid Aneurysms: An Experimental Study in a Canine Model", vol. 15, pp. 493–502, American Journal of Neuroradiology, Mar., 1994.

Baruch B. Lieber, et al., "Alteration of Hemodynamics in Aneurysm Models by Stenting: Influence of Stent Porosity", vol. 25, pp. 460–469, Annals of Biomedical Engineering, 1997.

* cited by examiner

Primary Examiner—Michael H. Thaler
(74) Attorney, Agent, or Firm—Fish & Neave; Nicola A. Pisano (57) ABSTRACT

Methods and apparatus for treating vascular abnormalities in highly tortuous vessels are provided comprising a stent having at least one end region that engages a first portion of a circumference of a vessel in a region adjacent to an abnormality to anchor the stent, and a mid-region that engages a second portion of the circumference of the vessel wall to span the abnormality, the second portion having a smaller circumferential extent than the first portion. The mid-region includes a plurality of members that span the abnormality and form a lattice that occludes the abnormality. A delivery system also is provided to deliver the stent within a parent artery and orient the mid-region of the stent to span the abnormality.

25 Claims, 5 Drawing Sheets

APPARATUS AND METHODS FOR SELECTIVELY STENTING A PORTION OF A VESSEL WALL

FIELD OF THE INVENTION

The present invention relates to apparatus and methods for treating abnormalities or disease states in tortuous vessels. In particular, this invention relates to stents and delivery systems used to selectively support portions of a vessel wall, such as for treating aneurysms and vascular dissections.

BACKGROUND OF THE INVENTION

Some forms of vascular abnormality or disease states, such as aneurysms and vascular dissections, affect only portions of a vessel. The term "abnormality," as used herein, refers to any damage or disease state that affects a portion of a vessel wall. An aneurysm, for example, is an area within an artery where the artery wall integrity has become compromised by age, disease or trauma. As a result, blood pressure within the artery causes a portion of the artery wall to bulge or balloon. The portion of the aneurysm attached to the undeformed wall of the parent artery is called the "neck," and the bulbous pouch of the aneurysm is called the "dome." The dome is considerably thinner and weaker than the undeformed parent artery wall, and therefore is much more prone to rupture.

A vascular dissection describes vessel damage in which a portion of a vessel wall delaminates, and a flap of vascular tissue may extend into and partially occlude blood flow in the parent artery. In each of these different types of vascular abnormalities, a portion of a vessel wall is damaged, but the remaining vessel wall is otherwise healthy.

Vascular abnormalities can rupture and result in debilitating injury or death, depending on the size and location of the rupture and the amount of extra-arterial bleeding. For example, an aneurysm located in the brain is called a cerebral aneurysm, and hemorrhagic stroke results when a cerebral aneurysm ruptures. In addition to the risk of stroke, large aneurysms located in certain regions of the brain may result in neurologic problems due to so called "mass effect." This effect is characterized by the enlarged blood filled dome pressing upon important areas of the brain, and may be manifested by symptoms such as seizure, or impaired speech or vision.

Previously known methods for treating cerebral aneurysms include extravascular and endovascular techniques. Extravascular methods require delicate brain surgery to place a clip across the neck of the aneurysm to effectively exclude the dome from blood flow through the undeformed parent artery. Such surgical treatments can be associated with high trauma, long recovery times, incomplete recovery of all neurologic functions, morbidity and mortality associated with open brain surgery. Additionally, aneurysms located in some extremely sensitive areas, such as those surrounding the brain stem, may be inoperable due to the high risk of mortality.

Endovascular techniques, in contrast, treat aneurysms using a microcatheter positioned within the aneurysm or the parent artery. U.S. Pat. No. 5,122,136 to Guglielmi et al. describes one such previously known endovascular technique using a device commonly called a "Guglielmi Detachable Coil" (GDC). A GDC comprises a soft pliable coil made from platinum or platinum alloy that is soldered to a stainless steel coil and push wire. The stainless steel coil and push wire are used to position the platinum coil in the dome of the aneurysm, and position the junction between platinum coil and stainless steel coil near the neck of the aneurysm. A direct current (DC) is applied to the push wire, stainless steel coil and platinum coil to form a thrombogenic mass within the dome and thereby occlude the aneurysm.

By exposing the junction between the platinum coil and its push wire coil to blood and continuing to apply electric current to the push wire, the exposed portion of the stainless steel coil electrolytically dissolves. The remaining portion of the stainless steel coil and push wire then may be withdrawn from the artery, leaving the platinum coil within the dome. Depending on the size of the aneurysm, many such coils (typically from 5 to 20) may need to be placed within the dome to prevent blood from entering the aneurysm. Because pressure on the fragile dome is reduced, the risk of rupture is eliminated or greatly reduced.

Endovascular treatment permits access to vascular lesions through percutaneous introduction of microcatheters through the femoral artery, and therefore involves less patient trauma than an open surgical approach. This often results in a faster recovery and reduced morbidity and mortality. Drawbacks of GDC techniques include patient selection issues—the neck of the aneurysm must be of a sufficient size and orientation to allow coil entry, but prevent coil migration after detachment. Because multiple devices often must be placed directly in the fragile dome, each device introduction risks rupturing the dome due to mechanical trauma induced by the device.

U.S. Pat. No. 5,135,536 to Hillstead describes a stent for treating occlusive vascular disease comprising an expandable wire tube having a reduced diameter for transluminal placement. Once the stent is positioned within a vessel, a balloon catheter is used to expand the stent to support and reinforce the full circumference of the vessel. Such prior art stents typically have high radial strength to resist collapse due to vessel disease. U.S. Pat. No. 5,314,444 to Gianturco describes a stent having similar construction and operation.

Such previously known devices are not suitable for treating vascular abnormalities, such as aneurysms, occurring in highly tortuous vessels. For example, previously known endovascular stents are designed to provide high radial strength when deployed, and therefore generally are too rigid to negotiate the tortuous anatomy of cerebral vessels. In addition, because a stent, once deployed, is often overgrown by thick layer of vessel endothelium, a phenomenon referred to as "neointimal hyperplasia," there is some reduction of the vessel flow area after placement of the stent. Such reduction in flow area may cause an unacceptable reduction of blood flow in cerebral arteries. Some researchers believe that the higher the percent coverage of an artery by a stent, the more hyperplasia will occur.

As a result of the drawbacks of previously known endovascular techniques, it is desirable to find an alternative solution for treating vessels. In Wakhloo et al., "Self-Expanding and Balloon-Expandable Stents in the Treatment of Carotid Aneurysms: An Experimental Study in a Canine Model," *Am. J. Neuroradiology*, 15:493–502 (1994), the authors describe the feasibility of placing a stent across a portion of the neck of an aneurysm to alter the hemodynamics and therefore induce spontaneous clotting of stagnant blood within the dome. Those authors further postulated that the struts of the stent covering the neck of the aneurysm may provide a lattice for the growth of new endothelial cells across the neck, permanently excluding it from blood flow through the parent artery. Shrinking the aneurysm and resorption of blood within the aneurysm are expected to follow, thus preventing long-term mass effect problems.

In view of the foregoing, it would be desirable to provide methods and apparatus to enable a stent to be atraumatically and transluminally inserted into highly tortuous vessels, such as the cerebral arteries.

It further would be desirable to provide methods and apparatus for deploying a stent that spans a portion of a vessel to provide a lattice for the growth of new endothelial cells across the portion.

It also would be desirable to provide methods and apparatus comprising a stent having sufficient radial strength to resist downstream migration within the parent artery, but which is less subject to narrowing of the vessel flow area.

SUMMARY OF THE INVENTION

In view of the foregoing, it is an object of this invention to provide methods and apparatus to enable a stent to be atraumatically and transluminally inserted into highly tortuous vessels, such as the cerebral arteries.

It is another object of this invention to provide methods and apparatus for deploying a stent that spans a portion of an vessel to provide a lattice for the growth of new endothelial cells across the portion.

It is a further object of the present invention to provide methods and apparatus comprising a stent having sufficient radial strength to resist downstream migration within the parent artery, but which is less subject to narrowing of the vessel flow area.

These and other objects of the present invention are accomplished by providing a stent and a delivery system for implanting the stent. The stent comprises at least one end region that engages a first portion of a circumference of a vessel in a region adjacent to a vessel abnormality to anchor the stent, and a mid-region that extends over a second portion of the circumference of the vessel to span the abnormality, the second portion having a smaller circumferential extent than the first portion. The mid-region includes a plurality of members that span the abnormality and form a lattice that occludes the abnormality. The lattice also may be covered with a graft material, such as expanded polytetra fluoroethylene (PTFE), or polyester mesh. Because the mid-region extends over the smaller second portion of the circumference, the stent is highly flexible and may result in reduced narrowing of the flow area of the parent artery.

In accordance with the principles of the present invention, a delivery system is provided comprising a catheter that enables the mid-region of the stent to span the abnormality. In a preferred embodiment, the catheter comprises a flexible outer catheter on which the stent is releasably mounted, and an inner torsional catheter that selectively engages the outer catheter to rotate the stent to a desired orientation.

Methods of using the stent and delivery catheter of the present invention are also provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention provides methods and apparatus for negotiating highly tortuous vessels to treat abnormalities located therein, without suffering from the drawbacks of previously known devices. More particularly, apparatus constructed in accordance with the principles of the present invention includes a stent having at least one end portion that engages a first portion of a circumference of a vessel to anchor the stent, and a mid-region having a plurality of members that extend over a second portion of the circumference of a vessel to span the abnormality, the second portion having a smaller circumferential extent than the first portion. Although the mid-region of the stent is highly flexible, care must be taken to orient the mid-region relative to the abnormality. Accordingly, a delivery system is provided for orienting the stent within the vessel during deployment.

Figure 1:
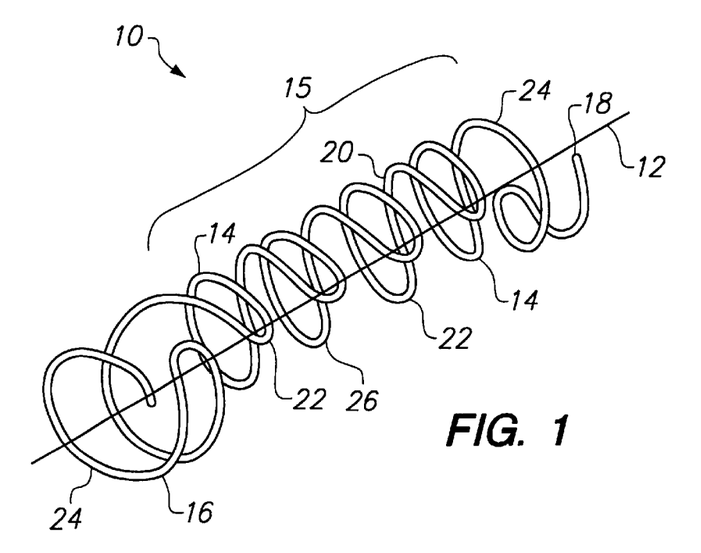
FIG. 1 is a perspective view of an illustrative embodiment of a stent constructed in accordance with the principles of the present invention.

Referring now to FIG. 1, an illustrative stent constructed in accordance with the principles of the present invention is described. Stent 10, shown in FIG. 1 in a deployed state, has a longitudinal axis 12, mid-region 15 comprising a plurality of elements 14, and first end 16 and second end 18. Elements 14 of mid-region 15 are formed of a plurality of curved sections 20 joined by a plurality of bends or cusps 22. First and second ends 16 and 18 include curved sections 24.

When deployed in a vessel, curved sections 24 and 20 preferably have a convex outer surface and engage a first portion and a second portion, respectively, of the circumference of the vessel, the second portion smaller than the first portion. As shown in FIG. 1, curved sections 24 engage a first portion equal to the full circumference of the vessel, whereas curved sections 20 engage a second portion less than the full circumference (e.g., one-quarter, one half or three-quarters, etc.). Curved sections 20 and 24 preferably are oriented generally perpendicularly to longitudinal axis 12.

Figure 2:
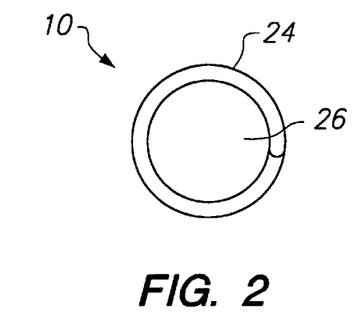
FIG. 2 is an end view of the stent of FIG. 1.
Figure 3:
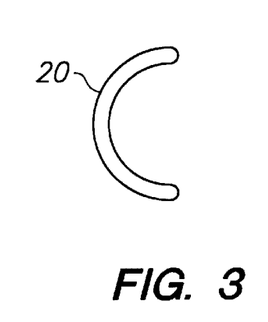
FIG. 3 is a side view of a member forming the mid-region of the stent of FIG. 1.

As illustrated in FIGS. 2 and 3, curved sections 24 form a tubular member having central opening 26, whereas curved sections 20, which have the same deployed diameter as curved sections 24, extend over only a portion of the circumference of the vessel. Accordingly, when stent 10 is deployed in a parent vessel, curved sections 24 at first and second ends 16 and 18 engage the interior surface of a parent vessel adjacent to the neck of the aneurysm, whereas curved sections 20 form a plurality of members that span the abnormality to promote clotting and endothelial growth. Advantageously, because mid-region 15 does not extend over the entire circumference of the vessel when deployed, stent 10 is highly flexible and provides less resistance to blood flow through the parent artery.

Stent 10 preferably is constructed of a shape-memory material such as nickel-titanium alloy (nitinol) having an austenite phase transition temperature slightly above body temperature. In this case, the stent may be cooled into the martensite phase and compressed to a reduced delivery diameter, and conditioned to undergo a heat-activated phase transformation to a deployed, expanded state when heated to a temperature slightly above body temperature. Alternatively, an electric current may be applied to heat the stent to a temperature at which it transitions to the austenite phase, and assumes an expanded shape. Alternatively, the transformation temperature may be set below body temperature, and the stent mechanically constrained.

Stent 10 may be formed, for example, by wrapping a nitinol wire around a mandrel template, and then conditioning the wire through a series of heat treatments in accordance with methods that are per se known. Alternatively, stent 10 may be fabricated from either nitinol or stainless steel tubing or sheets using previously known electron discharge machining (EDM), chemical etching, or laser cutting techniques. As a further alternative, stent 10 may be formed from a biocompatible or bioerodible polymer.

Figure 4:
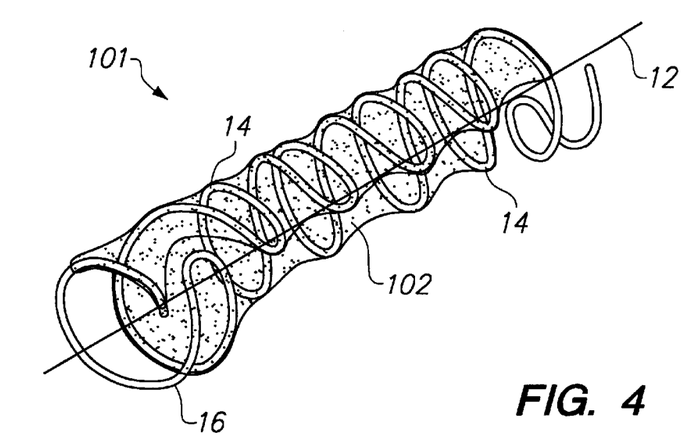
FIG. 4 is a perspective view of an alternative illustrative embodiment of a stent constructed in accordance with the principles of the present invention.

FIG. 4 illustrates an alternative embodiment of a stent constructed in accordance with the principles of the present invention. Stent 101 is similar to stent 10, but includes cover 102 that spans elements 14 and is disposed about a portion of the circumference of stent 101. Cover 102 may comprise a typical graft material, such as polyester or expanded PTFE, and may be applied to an exterior or interior surface of elements 14 using a biocompatible adhesive or sutures. When stent 101 is deployed in a parent vessel, cover 102 is oriented to span the abnormality to promote clotting and endothelial growth.

Figure 5:
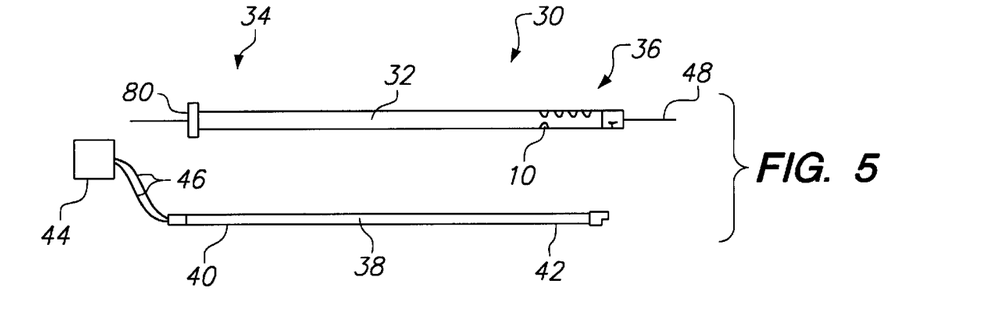
FIG. 5 is a side view of an illustrative embodiment of a delivery system constructed in accordance with the principles of the present invention.

Referring to FIG. 5, delivery system 30 for deploying a stent of the present invention is described. As will be readily apparent, the delivery system of the present invention advantageously may be used whenever it is desired to align a feature of a device with a region of a vessel. Delivery system 30 includes outer catheter 32 having proximal end 34 and distal end 36, inner torsion catheter 38 having proximal end 40 and distal end 42, and controller 44 coupled to proximal end of inner torsion catheter 38 by insulated wires 46.

Figure 6:
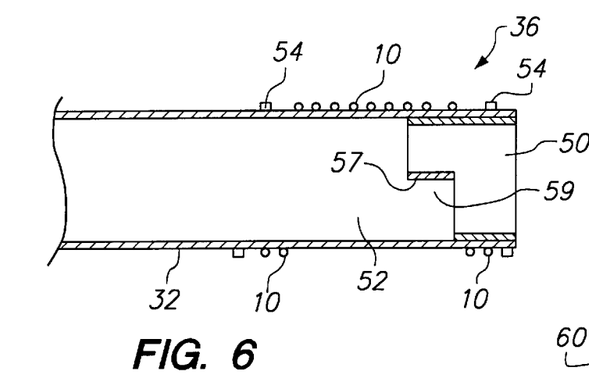
FIG. 6 is a sectional view of a distal end of an outer catheter of the delivery system of FIG. 5.
Figure 7:
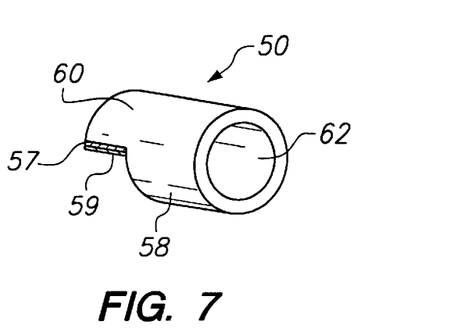
FIG. 7 is a perspective view, in isolation, of the first torsion gear of FIG. 6.

As illustrated in FIG. 6, outer catheter 32 preferably comprises a highly flexible material, such as polyethylene, silicone, nylon, polyester or polyurethane, having central lumen 52 that accepts guide wire 48 and has first torsion gear 50 mounted on distal end 36. First torsion gear 50, shown in isolation in FIG. 7, preferably comprises a radiopaque and conductive metal, metal composite or metal alloy, and includes cylindrical portion 58, stepped portion 60 having engagement surface 59, and lumen 62 extending through portions 58 and 60. Stent 10 is mounted adjacent to distal end 36 of catheter 32, and/or first torsion gear 50, for example, by a thermally activated adhesive or polymer, or electrically erodible wire. Alternatively, a retractable sheath could retain stent 10 on catheter 32, allowing stent 10 to expand when the sheath is retracted.

Distal end 36 of outer catheter 32 also preferably includes radio-opaque marker bands 54 disposed on outer surface 56, which may be used to identify the longitudinal location of stent 10 relative to the neck of a target aneurysm, and longitudinally-oriented marker band 57 on first torsion gear 50. Marker band 57 enables the physician to determine the circumferential orientation of stent 10 relative to the neck of an abnormality, as described in greater detail below.

Figure 8:
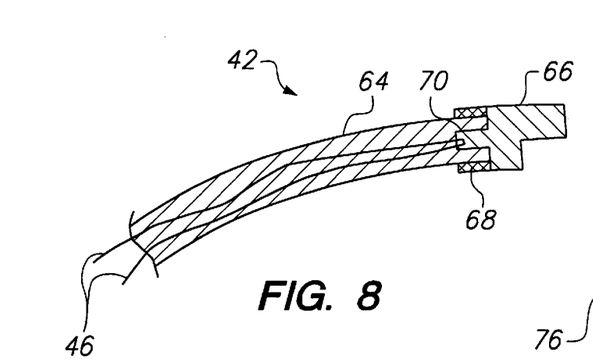
FIG. 8 is a sectional view of an inner torsion catheter of the delivery system of FIG. 5.

Referring to FIG. 8, distal end 42 of inner torsion catheter 38 is described. Inner torsion catheter 38 comprises tubular member 64 having second torsion gear 66 coupled to its distal end by clamp ring 68. Insulated wires 46 extend from second torsion gear 66 and through tubular member 64 to controller 44. Tubular member 64 is flexible in the longitudinal direction, but is sufficiently rigid to apply torque to second torsion gear 66. Tubular member 64 preferably comprises a combination of braided metal and metal alloy wires enclosed within a polymer jacket and lubricious coating, or alternatively, a helical coil and metal alloy wires covered with a polymer jacket and lubricious coating. Tubular member 64 includes a lumen or bore 70 for accepting a shank portion of second torsion gear 66.

Figure 9:
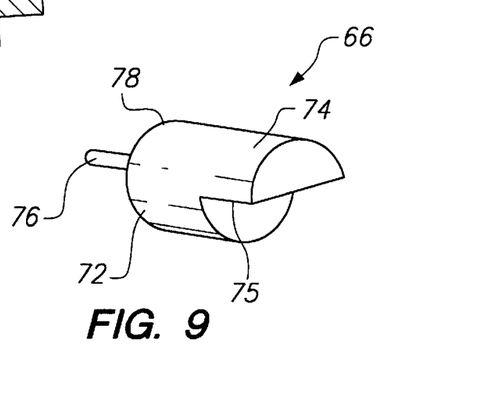
FIG. 9 is a perspective view of the second torsion gear of FIG. 8.

With respect to FIG. 9, second torsion gear 66, shown in isolation, includes cylindrical portion 72, stepped portion 74 having engagement surface 75, and shank 76 extending from end face 78 of cylindrical portion 72. Shank 76 fits within bore 70 of tubular member 64 so that when clamp ring 68 is applied, it secures tubular member 64 to shank 76.

Second torsion gear 66 preferably comprises an electrically conductive metal, metal composite or metal alloy that is resistively heated when a radio-frequency ("RF") power is applied from controller 44 through insulated wires 46. In this manner, second torsion gear 66 may be selectively resistively heated by controller 44, so that heat generated in second torsion gear 44 is conducted to and melts the thermally activated adhesive or polymer retaining stent 10 on outer catheter 32. Alternatively, second torsion gear may be configured to electrically couple to first torsion gear 50, to deliver power to an electrically erodible wire that retains stent 10 on outer catheter 32.

Figure 10:
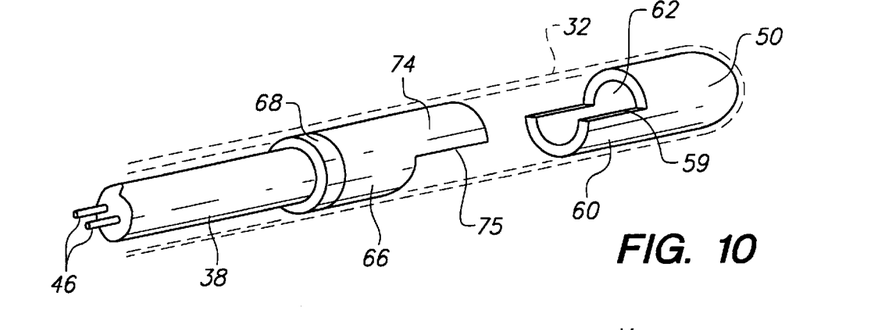
FIG. 10 is a partial cutaway view of the delivery system of FIG. 5.

As depicted in FIG. 10, engagement surface 75 of second torsion gear 66 is configured to engage engagement surface 59 of first torsion gear 50, so that rotation of inner torsion catheter 38 causes rotation of distal end 36 of catheter 32. Accordingly, inner torsion catheter enables mid-region 15 of stent 10 to be oriented so that it spans the neck of an aneurysm.

Figure 11A:
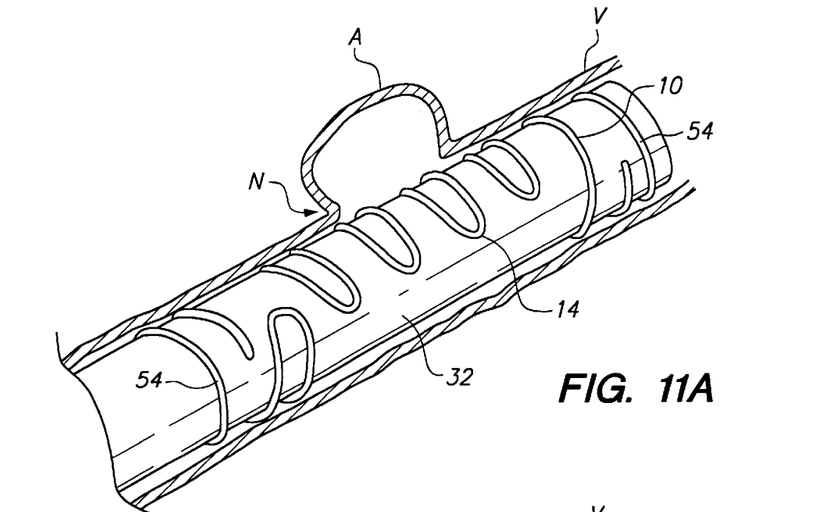
FIG. 11A is a partial sectional view of the stent of FIG. 1 and the delivery system of FIG. 5 disposed within a vessel.
Figure 11B:
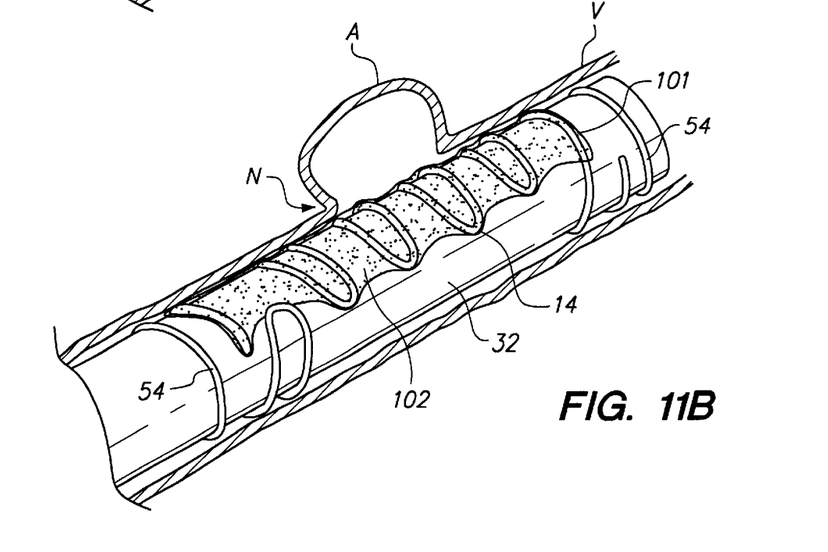
FIG. 11B is a partial sectional view of the stent of FIG. 4 and the delivery system of FIG. 5 disposed within a vessel.

Referring now to FIGS. 11A and 11B, illustrative methods of using the delivery system of FIG. 5 to deploy a preferred embodiment of the stent of the present invention are described. First, outer catheter 32 is percutaneously and transluminally advanced over a guide wire to dispose distal end 36 in a portion of vessel V containing aneurysm A using known radiological techniques. Once stent 10 is disposed across neck N of aneurysm A, for example, by determining the location of marker bands 54 with a fluoroscope, the guide wire is withdrawn.

Inner torsion catheter 38 is inserted through hemostatic coupling 80 of outer catheter 32 and then advanced and rotated until second torsion gear 66 engages with first torsion gear 50. Inner torsion catheter 38 is then rotated, for example, as guided by radio-opaque marker band 57, until the convex portion of mid-region 15 is aligned with and spans neck N of aneurysm A, as depicted in FIG. 11A. More specifically, rotation of inner torsion catheter 38 and outer catheter 32 may be as a unit. Alternatively, because outer catheter 32 is more flexible than inner torsion catheter 38, relative movement of inner torsion catheter 38 within outer catheter 32 may simply cause the distal end of the outer catheter to twist while the proximal end of outer catheter 32 remains stationary.

Controller 44 is then activated to cause an RF current to flow through second torsion gear 66. In an embodiment where stent 10 is affixed to distal end 36 of outer catheter 32 by a thermally activated adhesive or polymer, for example, a low temperature biocompatible wax, the RF power delivered to second torsion gear 66 causes resistive heating of the distal end of the catheter, thereby melting the thermally activated adhesive and permitting the stent to expand to its deployed diameter. Delivery system 30 is then withdrawn, leaving stent 10 with mid-region 15 disposed across neck N of aneurysm A. Stent 10 serves to alter the hemodynamics within aneurysm A to cause it to clot, and acts as a scaffold for endothelial growth that excludes aneurysm A from vessel V.

Alternatively, in an embodiment where stent 10 is retained on distal end 36 by an electrically erodible wire coupled to first torsion gear 50, RF power supplied by controller 44 may be delivered to and cause stent 10 to undergo a thermally activated phase change to expand to its deployed state. Applying additional power causes the erosion of the electrically erodible wire.

FIG. 11B illustrates deployment of stent 101 of FIG. 4. As shown in FIG. 11B, during deployment, inner torsion catheter 38 is rotated until cover 102 is aligned with and spans neck N of aneurysm A. Once stent 101 expands to its deployed diameter, cover 102 acts as a scaffold for endothelial growth that excludes aneurysm A from vessel V.

Other arrangements of insulating wires 46 and controller 44 will be apparent to one of skill in the art of interventional catheter design. For example, in other embodiments, other release mechanisms may be employed to release stent 10 from distal end 36 of outer catheter 32, such as the pull-wire arrangement described in U.S. Pat. No. 5,443,500 to Sigwart, which is incorporated herein by reference.

In still other embodiments, stent 10 may comprise an elastically expandable, plastically deformable or superelastic material, rather than thermally-activated material, and may be constructed using other shapes than the arcuate wire portions of the embodiment of FIG. 1.

Figure 12:
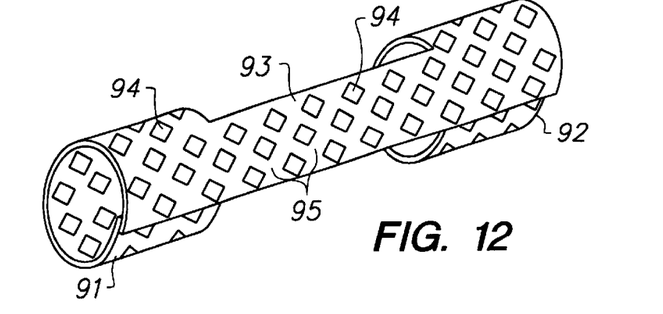
FIG. 12 is a perspective view of an alternative embodiment of the stent of the present invention.

For example, as depicted in FIG. 12, stent 10 may comprise first and second coil-sheet portions 91 and 92, respectively, such as described in the above-incorporated patent to Sigwart, interconnected by mid-region 93. Coil-sheet portions 91 and 92 and mid-region 93 preferably comprise a mesh having a plurality of openings 94, so that the lattice formed by openings 94 constitutes a plurality of intersecting members 95. Coiled sheet portions 91 and 92 may be wound to a reduced diameter for transluminal delivery, and then expanded (or permitted to self-expand) once positioned within a vessel so that mid-region 93 spans the abnormality. As shown in FIG. 12, when deployed, coiled-sheet portions 91 and 92 engage a first portion equal to the full circumference of the vessel, whereas mid-region 93 engages a second portion of the circumference, the second portion less than the first portion.

Figure 13:
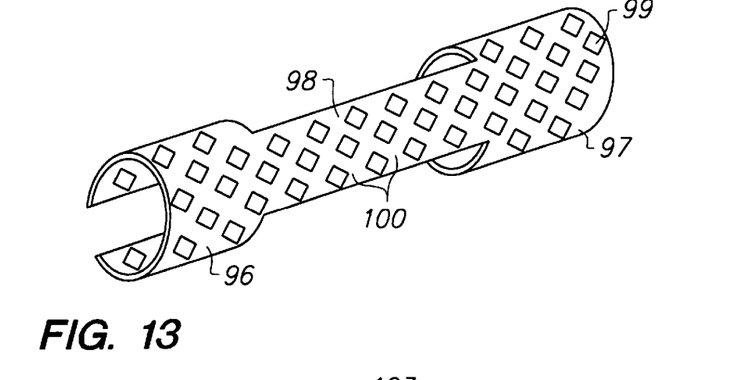
FIG. 13 is a perspective view of another alternative embodiment of the stent of the present invention.

As shown in FIG. 13, stent 10 alternatively may comprise first and second coiled expansile portions 96 and 97, respectively, interconnected by mid-region 98. Coil-ring portions 96 and 97 and mid-region 98 preferably comprise a mesh having a plurality of openings 99, so that the lattice formed by openings 99 constitutes a plurality of intersecting members 100. When deployed, coil-ring portions 96 and 97 engage a first portion less than a full circumference of the vessel, and mid-region 98 engages a second portion of the circumference, the second portion less than the first portion.

Figure 14:
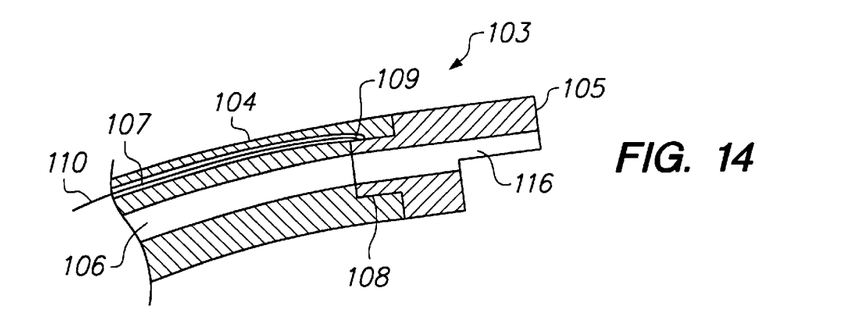
FIG. 14 is a sectional view of an alternative inner torsion catheter of the present invention.
Figure 15:
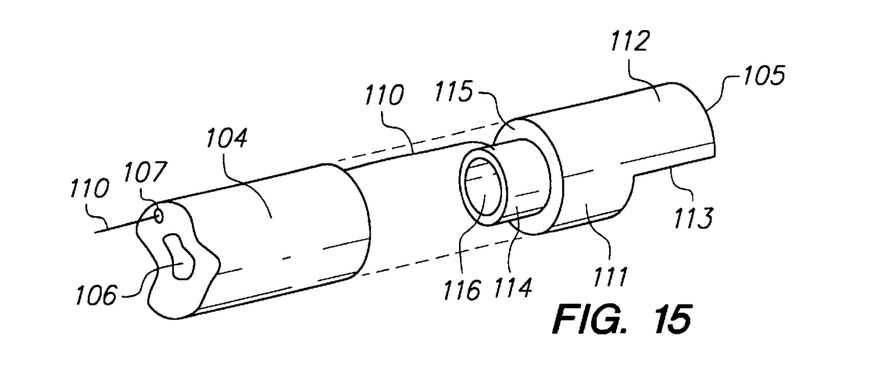
FIG. 15 is a partial cutaway view of the inner torsion catheter of FIG. 14.

For certain applications, it may be desirable to keep a guide wire or a guide wire tip in the vessel during stent placement. In particular, the guide wire or guide wire tip may provide additional stability during torquing of the inner and outer catheters. FIGS. 14 and 15 illustrate a distal end of an alternative embodiment of an inner torsion catheter that permits catheter delivery and deployment with a guide wire in the vessel.

As shown in FIG. 14, inner torsion catheter 103 comprises tubular member 104 having second torsion gear 105 coupled to its distal end. Tubular member 104 includes central lumen 106, peripheral lumen 107 and bore 108. Peripheral lumen 107 terminates at its distal end with opening 109 in a sidewall of bore 108. Insulated wires 110 (one shown in FIG. 14) extend from second torsion gear 105 and through peripheral lumen 107 to controller 44. Tubular member 104 is flexible in the longitudinal direction, but is sufficiently rigid to apply torque to second torsion gear 105. Tubular member 104 preferably comprises a combination of braided metal and metal alloy wires enclosed within a polymer jacket and lubricious coating, or alternatively, a helical coil and metal alloy wires covered with a polymer jacket and lubricious coating. Bore 108 accepts a shank portion of second torsion gear 105.

As shown in FIGS. 14 and 15, second torsion gear 105 includes cylindrical portion 111, stepped portion 112 having engagement surface 113, shank 114 extending from end face 115 of cylindrical portion 111 and lumen 116 extending through shank 114, cylindrical portion 111 and stepped portion 112. Shank 114 fits within bore 108 of tubular member 104 and is secured to tubular member 104 with a suitable adhesive, for example epoxy.

Second torsion gear 105 preferably comprises an electrically conductive metal, metal composite or metal alloy. Insulated wires 110 are electrically bonded to shank 114, such as by soldering or crimping. Second torsion gear 105 is resistively heated when RF power is applied from controller 44 through insulated wires 110.

Figure 16:
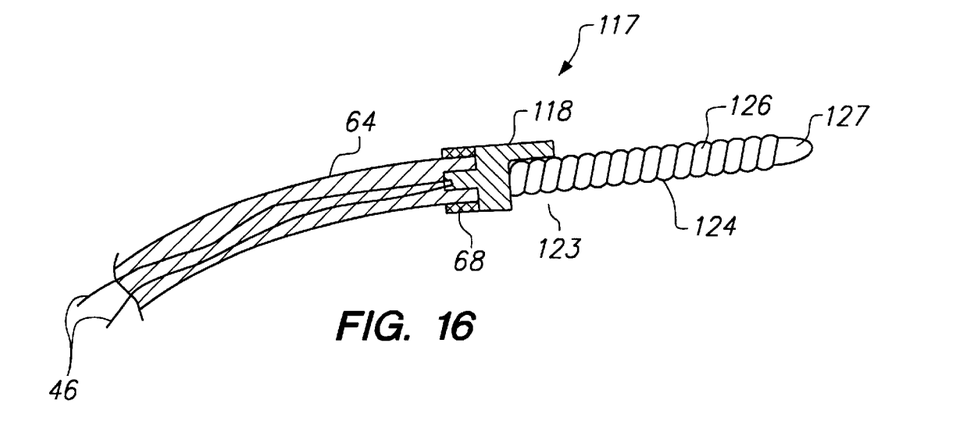
FIG. 16 is a sectional view of another illustrative inner torsion catheter of the delivery system of FIG. 5.
Figure 17:
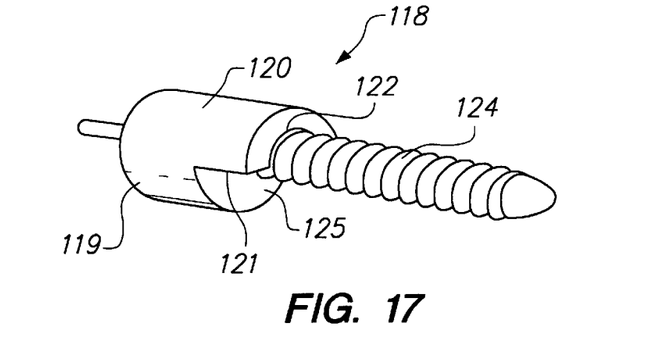
FIG. 17 is a perspective view of the second torsion gear of FIG. 16.
Figure 18:
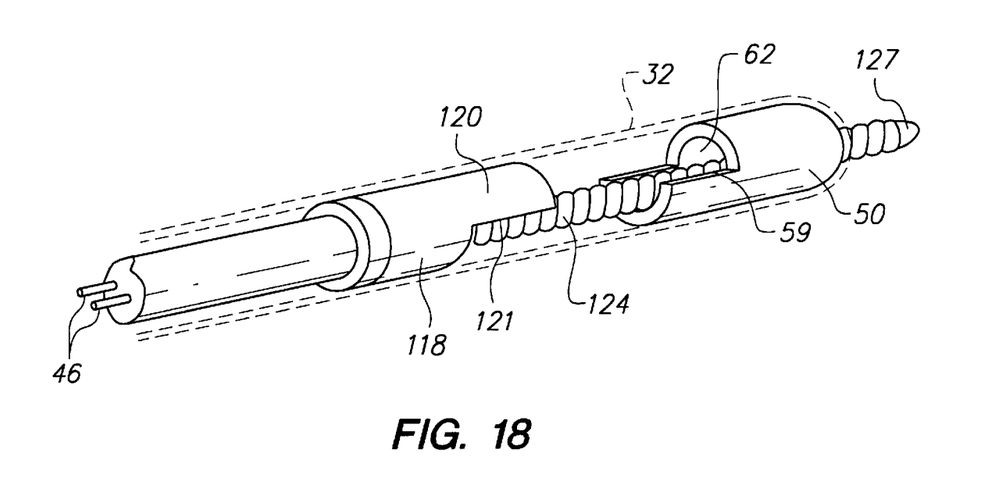
FIG. 18 is a partial cutaway view of the delivery system of FIG. 5 using the inner torsion catheter of FIG. 16.

FIGS. 16–18 illustrate a distal end of a further alternative embodiment of an inner torsion catheter having a guide wire tip. As shown in FIGS. 16 and 17, second torsion gear 118 includes cylindrical portion 119, stepped portion 120 having engagement surface 121 and semi-circular bore 122, and guide wire tip 124 extending from front face 125 of cylindrical portion 119. Guide wire tip 124 includes flexible coiled portion 126 and tapered tip 127. Proximal end 123 of guide wire tip 124 is engaged in semi-circular bore 122 of stepped portion 120. Coiled portion 126 preferably comprises an electrically insulative, flexible helical coil comprising a plastic or a metal alloy, such as stainless steel, having an electrically insulative cover. Tapered tip 127 may comprise a biocompatible material, such as nylon, disposed on the distal end of coiled portion 126. Alternatively, guide wire tip 124 may comprise a short section of a conventional stainless steel guide wire having an electrically insulative cover.

Second torsion gear 118 preferably comprises an electrically conductive metal, metal composite or metal alloy that is resistively heated when a radio-frequency RF power is applied from controller 44 through insulated wires 46. As shown in FIG. 18, engagement surface 121 of second torsion gear 118 is configured to engage engagement surface 59 of first torsion gear 50. Guide wire tip 124 extends through lumen 62 in first torsion gear 60.

Although preferred illustrative embodiments of the present invention are described above, a person of ordinary skill in the art will understand that various changes and modifications may be made without departing from the invention. Applicants intend that the appended claims cover all such changes and modifications that fall within the true spirit and scope of the invention.

What is claimed is:

1. Apparatus for treating an abnormality in a vessel, the apparatus comprising:
    a tubular member including an end region configured to circumferentially engage a first portion of the vessel adjacent to the abnormality;
    a mid-region of the tubular member comprising a plurality of members having a convex outer surface that is configured to engage a second portion of the vessel, the second portion being circumferentially smaller than the first portion and less than a full circumference of the vessel, the plurality of members adapted to span the abnormality; and
    a delivery system comprising a first catheter having a distal end adapted to support the tubular member and the mid-region, the first catheter having a lumen and a first gear disposed within the lumen for orienting the mid-region so that it spans the abnormality,
    wherein a retractable sheath retains the tubular member on the first catheter.

2. The apparatus of claim 1 wherein the tubular member comprises arcuate portions interconnected by a plurality of bends or cusps.

3. The apparatus of claim 1 wherein the tubular member has a longitudinal axis, the plurality of members oriented generally perpendicular to the longitudinal axis.

4. The apparatus of claim 1 wherein the tubular member comprises a coiled sheet.

5. The apparatus of claim 4 wherein the coiled sheet and mid-region comprises a plurality of openings.

6. The apparatus of claim 1 wherein the first portion is substantially equal to the full circumference of the vessel.

7. The apparatus of claim 1 wherein the first portion is less than the full circumference of the vessel.

8. The apparatus of claim 1 wherein the plurality of members engage one-half of the circumference of the vessel.

9. The apparatus of claim 1 wherein the tubular member further comprises a shape memory metal alloy or biocompatible polymer.

10. The apparatus of claim 1 further comprising a graft material covering the mid-region.

11. The apparatus of claim 1, wherein the first gear comprises a lumen that permits a guide wire to extend beyond the distal end of the first catheter into the vessel.

12. The apparatus of claim 1 further comprising a second catheter configured for insertion into the lumen of the first catheter, the second catheter having a distal end and a second gear disposed on the distal end, the second gear configured to engage the first gear when the second catheter is inserted in the lumen.

13. The apparatus of claim 12, wherein: p1 the second gear comprises a guide wire tip; and
    the first gear comprises a lumen that permits the guide wire tip to extend beyond the distal end of the first catheter into the vessel.

14. Apparatus for deploying a prosthesis to treat a region of a vessel, the prosthesis having a feature that is adapted to be aligned with the region, the apparatus comprising:
    a flexible catheter having a distal end adapted to support the prosthesis, a lumen and a first gear disposed within the lumen, the first gear rotating the flexible catheter to orient the feature so that it is aligned with the region;
    a torsion catheter configured for insertion into the lumen of the flexible catheter, the torsion catheter comprising an electrical conductor, a distal end, and a second gear disposed on the distal end, the second gear configured to engage the first gear when the torsion catheter is inserted in the lumen; and
    a controller that supplies radio-frequency power to the second gear via the electrical conductor.

15. The apparatus of claim 14, wherein the first gear comprises a lumen that permits a guide wire to extend beyond the distal end of the flexible catheter into the vessel.

16. The apparatus of claim 14, wherein:
    the second gear comprises a guide wire tip; and
    the first gear comprises a lumen that permits the guide wire tip to extend beyond the distal end of the flexible catheter into the vessel.

17. The apparatus of claim 14, wherein:
    the first gear comprises a cylindrical portion and a stepped portion having an engagement surface; and
    the second gear comprises a cylindrical portion and a stepped portion having an engagement surface that mates with the engagement surface of the first gear.

18. The apparatus of claim 14, wherein the first gear further comprises a longitudinally-oriented marker band.

19. The apparatus of claim 14 wherein the prosthesis is mounted on the catheter by a thermally activated adhesive or polymer.

20. The apparatus of claim 14 wherein the prosthesis is mounted on the catheter by an electrically erodible wire.

21. Apparatus for deploying a prosthesis to treat a region of a vessel, the prosthesis having a feature that is adapted to be aligned with the region, the apparatus comprising:
    a flexible catheter having a distal end adapted to support the prosthesis, a lumen and a first gear disposed within the lumen, the first gear rotating the flexible catheter to orient the feature so that it is aligned with the region,
    wherein a retractable sheath retains the prosthesis on the catheter.

22. A method of treating an abnormality at a treatment site within a vessel, the method comprising:
    providing a stent having a tubular end region comprising at least one curved section having a convex outer surface that is configured to engage a first portion of the vessel, and a mid-region comprising a plurality of members having a convex outer surface that is configured to engage a second portion of the vessel, the second portion being circumferentially smaller than the first portion and less than a full circumference of the vessel;

providing a delivery system for deploying the stent, the delivery system comprising a first catheter having a distal end configured to support the stent, a lumen, and a first gear disposed within the lumen, and a second catheter having a proximal end, a distal end, and a second gear disposed on the distal end;

transluminally disposing the stent at the treatment site;

inserting the second catheter into the lumen of the first catheter;

engaging the second gear with the first gear;

aligning the mid-region of the stent so that the plurality of members span the abnormality, by rotating a proximal end of the second catheter using the first gear to rotate the distal end of the first catheter;

providing a controller that outputs a radio-frequency power; and coupling the controller to the second catheter to release the stent from the distal end of the first catheter.

23. The method of claim 22 wherein a thermally activated adhesive or polymer retains the stent on the first catheter, and coupling the controller to the second catheter to release the stent from the distal end of the first catheter further comprises selectively resistively heating a portion of the first catheter to melt the adhesive or polymer to release the stent from the first catheter.

24. The method of claim 22 wherein an electrically erodible wire retains the stent on the first catheter, and coupling the controller to the second catheter to release the stent from the distal end of the first catheter further comprises delivering electrical power to the electrically erodible wire to release the stent from the first catheter.

25. A method of treating an abnormality at a treatment site within a vessel, the method comprising:

providing a stent having tubular end region comprising at least one curved section having a convex outer surface that is configured to engage a first portion of the vessel, and a mid-region comprising a plurality of members having a convex outer surface that is configured to engage a second portion of the vessel, the second portion being circumferentially smaller than the first portion;

providing a delivery system for deploying the stent, the delivery system comprising a first catheter having a distal end configured to receive the stent, a lumen, and a first gear disposed within the lumen;

transluminally disposing the stent at the treatment site;

aligning the mid-region of the stent so that the plurality of members span the abnormality by operating the first gear to rotate the distal end of the first catheter, and wherein a retractable sheath retains the stent on the first catheter; and retracting the sheath to release the stent from the first catheter.

\* \* \* \* \*